United States Patent [19]

Molaire

[11] Patent Number: 4,767,883

[45] Date of Patent: Aug. 30, 1988

[54] POLYMERIZABLE CYCLOHEXYLENEOXYALKYL ACRYLATES

[75] Inventor: Michel F. Molaire, Rochester, N.Y.

[73] Assignee: Eastman Kodak Company, Rochester, N.Y.

[21] Appl. No.: 77,712

[22] Filed: Jul. 24, 1987

[51] Int. Cl.$^4$ .............................................. C07C 69/52
[52] U.S. Cl. .................................... 560/220; 560/224
[58] Field of Search ........................................ 560/220

[56] References Cited

U.S. PATENT DOCUMENTS

| | | | |
|---|---|---|---|
| 3,832,176 | 8/1974 | Verstraete et al. | 96/67 |
| 4,220,582 | 9/1980 | Orlowski et al. | 524/791 |
| 4,304,838 | 12/1981 | Hasegawa et al. | 430/253 |
| 4,322,490 | 3/1982 | Molaire | 430/281 |
| 4,619,890 | 10/1986 | Molaire et al. | 430/495 |

Primary Examiner—Paul J. Killos
Attorney, Agent, or Firm—William J. Davis

[57] ABSTRACT

A cyclohexyleneoxyalkyl acrylate monomer having the structural formula:

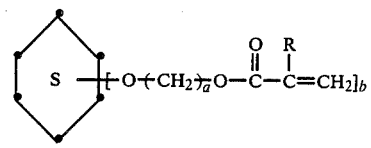

wherein
R is H or $CH_3$,
a is an integer of from 1 to 10 and
b is 1 or 2 is useful in polymerizable compositions.

5 Claims, No Drawings

POLYMERIZABLE CYCLOHEXYLENEOXYALKYL ACRYLATES

CROSS REFERENCE TO RELATED APPLICATIONS

Reference is hereby made to commonly-assigned U.S. patent applications Ser. No. 07/077,715 entitled PHOTORESIST COMPOSITION COMPRISING CYCLOHEXYLENEOXYALKYL ACRYLATES filed in the names of G. W. Klein, R. C. McConkey, M. F. Molaire and J. M. Noonan concurrently herewith, and Ser. No. 07/077,714 entitled LAMINATE FOR THE FORMATION OF BEAM LEADS FOR IC CHIP BONDING filed in the names of G. W. Klein, R. C. McConkey, M. F. Molaire and J. M. Noonan concurrently herewith.

BACKGROUND OF THE INVENTION

1. Field of the Invention

This invention relates to polymerizable monomers having utility in polymerizable compositions.

2. Descriptions of the Prior Art

Specialized uses of polymerizable compositions such as photoresists often require a unique combination of properties. In some applications, it is desirable that the monomers in such compositions have a low viscosity and be capable of forming polymers having a high glass transition temperature (Tg). Further, it is often desirable that the polymerized composition be flexible and nonbrittle. Considerable difficulties have been encountered in developing a polymerizable composition that has all of these properties.

Photopolymerizable compositions comprising benzoyloxyalkyl acrylates are described in U.S. Pat. No. 4,322,490.

U.S. Pat. No. 3,832,176 discloses a photoresist layer formed of a photopolymerizable composition comprised of a bisacryloyl monomer, such as 1,4-bis(methacryloyloxymethyl)cyclohexane. Such monomers, however, have higher viscosities than the monomers of this invention and produce photopolymerized compositions which tend to be more brittle and less flexible.

SUMMARY OF THE INVENTION

In accordance with the present invention, there is provided a polymerizable monomer having a low viscosity and being capable of forming a polymer having a high Tg which is particularly useful in providing flexible and nonbrittle polymerizable compositions.

The polymerizable monomer has the structural formula:

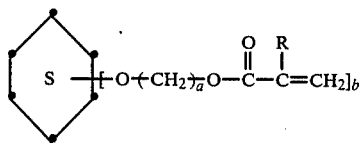

wherein
R is H or CH$_3$,
a is an integer of from 1 to 10 and
b is 1 or 2.

DESCRIPTION OF THE PREFERRED EMBODIMENTS

The monomers of this invention are polymerizable and crosslinkable with heat or upon exposure to radiant energy such as UV light and thus are useful in heat polymerizable and photopolymerizable compositions. The monomers described herein are useful in a variety of applications, such as in lithographic printing plate and photoresist compositions. Further, the monomers are useful in non-imaged polymerized coatings, such as in the polymerized crosslinked homopolymer smoothing layer for the optical recording element described in U.S. Pat. No. 4,619,890, issued Oct. 28, 1986, in the names of M. F. Molaire and M. S. Kaplan.

In accordance with this invention, there is provided a monomer having the structural formula set forth in the summary above. Particularly preferred monomers are those wherein a is 1 to 6 and b is 2. Another preferred class of monomers are those wherein a is 2 to 6.

The following cyclohexyleneoxyalkyl acrylate monomers illustrate this invention:
cyclohexyleneoxymethyl acrylate,
cyclohexyleneoxymethyl methacrylate,
cyclohexyleneoxyethyl acrylate,
cyclohexyleneoxyethyl methacrylate,
cyclohexyleneoxypropyl acrylate,
cyclohexyleneoxypropyl methacrylate,
cyclohexyleneoxybutyl acrylate,
cyclohexyleneoxybutyl methacrylate,
cyclohexyleneoxypentyl acrylate,
cyclohexyleneoxypentyl methacrylate,
cyclohexyleneoxyhexyl acrylate,
cyclohexyleneoxyhexyl methacrylate,
1,4-cyclohexylenebis(oxymethyl) diacrylate,
1,4-cyclohexylenebis(oxymethyl) dimethacrylate,
1,4-cyclohexylenebis(oxyethyl) diacrylate,*
1,4-cyclohexylenebis(oxyethyl) dimethacrylate,
1,4-cyclohexylenebis(oxypropyl) diacrylate,
1,4-cyclohexylenebis(oxypropyl) dimethacrylate,
1,4-cyclohexylenebis(oxybutyl) diacrylate,
1,4-cyclohexylenebis(oxybutyl) dimethacrylate,
1,4-cyclohexylenebis(oxypentyl) diacrylate,
1,4-cyclohexylenebis(oxypentyl) dimethacrylate,
1,4-cyclohexylenebis(oxyhexyl) diacrylate,
1,4-cyclohexylenebis(oxyhexyl) dimethacrylate.
*Alternatively named 1,4-bis(acryloyloxyethoxy)cyclohexane The monomers of this invention can be prepared by reacting acryloyl chloride or methacryloyl chloride with an hydroxyalkoxycyclohexane in a suitable solvent such as dichloromethane. Exemplary hydroxyalkoxycyclohexanes include
hydroxymethoxycyclohexane,
hydroxyethoxycyclohexane,
hydroxypropoxycyclohexane,
hydroxybutoxycyclohexane,
hydroxypentoxycyclohexane,
hydroxyhexylcyclohexane,
1,4-bis(hydroxymethoxy)cyclohexane,
1,4-bis(hydroxyethoxy)cyclohexane,
1,4-bis(hydroxypropoxy)cyclohexane,
1,4-bis(hydroxybutoxy)cyclohexane,
1,4-bis(hydroxypentoxy)cyclohexane, and
1,4-bis(hydroxyhexyloxy)cyclohexane.

The hydroxyalkoxycyclohexanes are known compounds and/or can be prepared by methods known in the art. Generally, the hydroxyalkoxycyclohexane can be prepared by hydrogenating the corresponding hydroxyalkoxybenzene. For example, 1,4-bis(hydroxyethoxy)cyclohexane can be prepared by hydrogenating 1,4-bis(hydroxyethoxy)benzene preferably in the presence of a catalyst such as rhodium.

The hydroxyalkoxybenzene can be prepared by reacting a phenol with a halogenated alcohol in the presence of $K_2CO_3$ or KI. For example, 1,4-bis(hydroxyethoxy)benzene can be prepared by reacting hydroquinone with 2-chloroethanol.

Example 1 which follows, although specific for 1,4-cyclohexylenebis(oxyethyl)diacrylate is a general procedure that can be used to prepare the monomers of this invention.

The monomers of this invention have a low viscosity and are capable of forming polymers having a high Tg. The improved flexibility and reduced brittleness of compositions containing polymerized monomers of this invention are believed to result at least partly from the oxy linkage(s) adjacent the saturated cyclohexane nucleus present in addition to the acrylate group, and from the ability of the cyclohexane nucleus to readily adopt various stereoscopic conformations.

As noted, the monomers of this invention have utility in a wide variety of applications. For example, the monomers are particularly useful in the photoresist compositions described in commonly-assigned U.S. patent application Ser. No. 07/077,715 entitled PHOTORESIST COMPOSITION COMPRISING CYCLOHEXYLENEOXYALKYL ACRYLATES noted above, and in flexible elements adapted for microelectronic and photofabrication elements, such as the laminate described in commonly-assigned U.S. patent application Ser. No. 07/077,714 entitled LAMINATE FOR THE FORMATION OF BEAM LEADS FOR IC CHIP BONDING noted above. Additionally, the monomers are useful in solventless coating compositions and in high speed coating applications due to their unique combination of properties described above.

The following Examples further illustrate the invention.

EXAMPLE 1

Preparation of 1,4-cyclohexylenebis(oxyethyl) diacrylate (HECK)

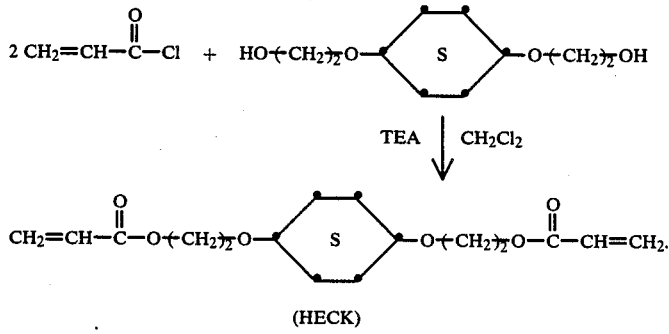

(HECK)

A 5 liter flask charged with 715 g (3.5 moles) of 1,4-bis(hydroxyethoxy)cyclohexane (HEC) and 730 g (7.2 moles) of triethylamine (TEA) in 1 liter $CH_2Cl_2$ was rapidly stirred and cooled in an ice bath. 633.6 g (7.0 moles) acryloyl chloride dissolved in 500 ml $CH_2Cl_2$ was added dropwise to the HEC solution. After the addition was completed, the flask was removed from the ice bath, and TEA.HCl was filtered off. The remainder was washed in 500 ml $CH_2Cl_2$. The organic solution was washed twice with each of 1 l 5% NaOH, 1 l 5% HCl and 1 l distilled $H_2O$. An emulsion formed in the organic layer from which a solid was filtered. The organic layer was dried with $MgSO_4$, suction filtered, and the $CH_2Cl_2$ was flash evaporated. The compound was air dried. Yield=704 g (65% theory). Analysis % calc.-/found C/61.5/61.8 H/7.7/7.9 O/30.7/30.7. High resolution NMR confirmed the structure.

HECK, a preferred monomer of this invention, exhibited a viscosisty of about 16 centipoise at room temperature. Tris(2-acryloyloxyethyl)-1,3,5-benzenecarboxylate, a prior art acrylate described in U.S. Pat. No. 4,322,490, exhibited a viscosity of about 4000 centipoise at room temperature.

EXAMPLE 2

Utility in Solventless Photopolymerizable Composition

The following formulation was spin coated at 3000 RPM onto a poly(ethylene terephthalate) support, having thereon a thin layer of metallic copper, and air dried.

| FORMULATION | |
|---|---|
| HECK | 7.5 g |
| tris(2-acryloyloxyethyl)-1,3,5-cyclohexylene tricarboxylate | 7.5 g |
| 3-benzoyl-5,7-dipropoxy coumarin (sensitizer) | 0.575 g |
| ethyl p-dimethylamino benzoate (activator) | 1.15 g |
| Fluorad FC431 (a nonionic fluorochemical surfactant sold by 3M) | 1 drop |

Polymerization and crosslinking was accomplished by exposing the coating through a Kodak T-14 Control Scale to an Oriel light source for 90 seconds at room temperature. The composition exhibited good photographic speed.

The invention has been described in detail with particular reference to preferred embodiments thereof, but it will be understood that variations and modifications can be effected within the spirit and scope of the invention.

What is claimed is:

1. A monomer having the structural formula

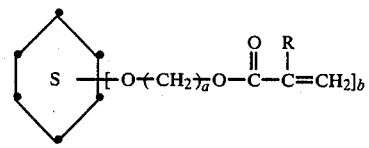
wherein
R is H or CH$_3$,
a is an integer of from 1 to 10 and
b is 1 or 2.
2. The monomer of claim 1 wherein a is 1 to 6.
3. The monomer of claim 1 wherein b is 2.
4. The monomer of claim 1 wherein both a and b are 2.
5. As a novel composition of matter, the compound 1,4-cyclohexylenebis(oxyethyl) diacrylate.
* * * * *